(12) United States Patent
Schmidt et al.

(10) Patent No.: US 10,299,900 B2
(45) Date of Patent: May 28, 2019

(54) BRUSH HEAD FOR AN ELECTRICALLY DRIVEN TOOTHBRUSH

(71) Applicant: M+C Schiffer GmbH, Neustadt/Wied (DE)

(72) Inventors: Eric Schmidt, Waldbreitbach (DE); Erwin Buchholz, Asbach (DE)

(73) Assignee: M+C SCHIFFER GMBH, Neustadt/Wied (DE)

( * ) Notice: Subject to any disclaimer, the term of this patent is extended or adjusted under 35 U.S.C. 154(b) by 157 days.

(21) Appl. No.: 15/347,106

(22) Filed: Nov. 9, 2016

(65) Prior Publication Data

US 2017/0128178 A1    May 11, 2017

(30) Foreign Application Priority Data

Nov. 9, 2015 (EP) .................................. 15193697

(51) Int. Cl.
| | |
|---|---|
| *A61C 17/22* | (2006.01) |
| *A46B 3/06* | (2006.01) |
| *A46B 13/00* | (2006.01) |
| *A46B 5/00* | (2006.01) |

(52) U.S. Cl.
CPC .............. *A61C 17/222* (2013.01); *A46B 3/06* (2013.01); *A46B 13/008* (2013.01); *A46B 5/0095* (2013.01); *A46B 13/00* (2013.01); *A46B 2200/1066* (2013.01)

(58) Field of Classification Search
CPC ..... A61C 17/222; A61C 17/3436; A46B 9/08; A46B 9/04; A46B 13/008; A46B 3/06; A46B 13/02; A46B 13/00
USPC .......................................... 15/21.1, 22.1, 28
See application file for complete search history.

(56) References Cited

U.S. PATENT DOCUMENTS

| | | | |
|---|---|---|---|
| 8,166,601 B2 * | 5/2012 | Brown, Jr. ............. | A46B 9/025 15/167.1 |
| 2010/0088836 A1 * | 4/2010 | Kirchhofer .......... | A46B 5/0025 15/167.1 |
| 2013/0139337 A1 | 6/2013 | Fritsch et al. | |

FOREIGN PATENT DOCUMENTS

EP           2599403 A1      6/2013

* cited by examiner

*Primary Examiner* — Laura C Guidotti
(74) *Attorney, Agent, or Firm* — The Webb Law Firm

(57) ABSTRACT

A brush head for an electrically driven toothbrush includes a holding part (2) that provides at least one connecting element for mechanically coupling the brush head to the electric drive of the toothbrush, wherein the holding part (2) integrally forms a stud (4) defining a pivot axis (S) about which the brush head is pivotable, and a plate (6) which at its end facing away from the stud (4) carries at least one bristle bundle (8) which at its attachment-side end includes a thickening (14) formed by surface melting. For improving the brush head, a substantially disc-shaped bristle carrier (10) is connected to a holding part (2) and includes a bore that is penetrated by the bristle bundle (8).

22 Claims, 6 Drawing Sheets

BRUSH HEAD FOR AN ELECTRICALLY DRIVEN TOOTHBRUSH

CROSS REFERENCE TO RELATED APPLICATION

This application claims priority to European Patent Application No. EP 15193697.8, filed on Nov. 9, 2015, which is hereby incorporated by reference as if set forth in its entirety herein.

BACKGROUND OF THE INVENTION

Field of the Invention

The present invention relates to a brush head for an electrically driven toothbrush. Such a brush head is commonly sold as a component of an attachment part which can be connected to a handpiece of the electrically driven toothbrush that commonly accommodates the drive in itself. The attachment part is an expendable item and made from plastic material. The attachment part usually comprises a sleeve member which is penetrated by a drive shaft that can be connected to a drive shaft of the handpiece. Disposed at the free end of the sleeve member is commonly the brush head according to the present invention.

Description of Related Art

Cleaning elements for the oral cavity are generally subject to the demand of having them be designed very compact and in space-saving manner since the space in the oral cavity is limited, where cleaning buccal tooth surfaces is difficult anyway due to the cheek being in the immediate vicinity.

There are various options for attaching bristle bundles, which are usually used for tooth cleaning, to a bristle carrier. The Inmold Method, in which a thickening is formed on the bristle bundle and sealed with liquid plastic material which forms the bristle carrier or at least a part thereof, allows the production of brushes which are relatively small in height. Height within the meaning of the present invention is there understood to be the extension substantially parallel to the filaments of the bristle bundles.

Technical plastic materials are generally not suitable for the Inmold Method due to their high viscosity under processing conditions. However, such technical plastic materials are commonly used to form a stud of the brush head which interacts with the shaft of the attachment part in order to impart the rotational or pivotal motion of the brush head during cleaning.

SUMMARY OF THE INVENTION

The present invention is based on the problem of providing an improved brush head for an electrically driven toothbrush.

To solve this problem, the present invention proposes a brush head having the features described in detail herein. It is a brush head for an electrically driven toothbrush. This brush head has a holding part that provides at least one connecting element for mechanically coupling the brush head to the electric drive of the toothbrush. The holding part has a stud which defines a pivot axis of the brush head. The holding part is commonly located entirely or in part within the aforementioned sleeve member of the attachment part and is accommodated therein in such a manner that the brush head can perform a rotational or pivotal motion relative to the sleeve member but is captively coupled to the sleeve member. The connecting element for mechanically coupling the brush head to the electric drive is in the simplest case a receptacle provided on the stud in which the drive shaft of the attachment part engages in order to impart, for example, a cyclic pivotal motion relative to the sleeve member onto the brush head. The connecting element is in this case located on the outer circumferential surface of the holding part, i.e. is in its extension perpendicular relative to the pivot axis defined by the holding part recessed in the commonly cylindrical stud. At its free end, the stud usually comprises a centering bore which interacts with a centering pin of the sleeve member to define a bearing for the pivotal motion of the brush head. On the side which is usually opposite the connecting element, the stud regularly has a locking recess into which a locking pin being fixedly connected to the sleeve member engages in order to secure the brush head within the sleeve member in such a manner that the brush head cannot be pulled along the pivot axis out from a receptacle formed on the sleeve member for the stud. The shaft provided in the sleeve member for coupling to the stud preferably comprises a substantially cylindrical locking head, the cylinder axis of which extends approximately parallel to the pivot axis of the locking pin. For accommodating this locking pin, the centrical stud typically comprises a locking pin receptacle provided eccentrically relative to the pivot axis, but in parallel extension thereto.

The previously discussed elements of the stud are after mounting the latter onto the sleeve member usually disposed within the sleeve member.

The centrical stud is radially protruded by a plate which according to the invention is provided as a component of the holding part. The holding part is accordingly composed of the centrical stud and the plate. The plate usually has a base surface that substantially corresponds to and/or runs parallel to the base surface of the surface of the brush head penetrated by the cleaning elements of the brush head. This surface can be circular or oval. The base surface of the surface, i.e., the contour thereof, is selected with a convex circumferential edge to protect the tender oral mucosa from damage.

The brush according to the invention in a manner known per se comprises at least one bristle bundle which is supported by the plate at its end facing away from the stud and in this direction protrudes over the plate. The bristle bundle at its attachment-side end comprises a thickening which is formed by surface melting and by way of which the bristle bundle is attached to the brush head by insert molding. The bristle bundle is then attached using the Inmold technology. In addition to a bristle bundle having at least one, commonly several filaments, other cleaning elements can also be provided on the brush head and connected to the brush head by insert molding, or are subsequently attached to the solidified plastic material by way of other connections, for example, by snapping, soldering or gluing them on.

The brush head also comprises a substantially disc-shaped bristle carrier. The bristle carrier usually has a base surface which corresponds to the surface penetrated by the bristle bundle. The disc-shaped bristle carrier regularly forms this surface, i.e. forms the upper end of the brush head. The bristle carrier is disc-shaped, i.e. has substantially co-planar main surfaces, where one of which usually forms the surface of the brush head and the other is provided disposed opposite to the plate and regularly in parallel extension thereto. The bristle carrier is designed as a relatively thin disc with a thickness between 0.5 and 3.0 mm. The bristle carrier has a bore to the bristle bundle which is penetrated by the bristle bundle. The thickening formed by surface melting is located on the rear side of the bristle carrier. The thickening protrudes radially over the bore so that the bristle bundle is due to the end-side thickening locked relative to the bristle carrier in a positive-fit manner and secured against being pulled out. The thickening can directly abut the mouth of the bore. The plate can in correspondence to the position of the respective thickening comprise a recess receiving the corresponding thickening, which enhances a compact design of the brush head.

The bristle carrier is connected to the holding part, for example, in such a manner that no gap extending in the height direction exists between the bristle carrier and the plate. The bristle carrier can abut directly against the plate. The bristle carrier and the holding part are there commonly shaped as two components that are initially produced separately and subsequently joined. This connection can be effected by welding, for example, ultrasound or frictional engagement.

The bristle carrier can also be connected to the plate with the interposition of an intermediate layer which partially or completely accommodates the thickening. This intermediate layer can be an adhesive layer. It can also be produced by injection molding.

In this case, the bristle carrier and the holding part are first produced as separate components, where the bristle carrier is provided with the bristle bundle(s). The components thus prepared are inserted into an injection mold and held spaced apart from each other so that the thickening of the bristle bundle is disposed between the upper side of the plate and the underside of the bristle carrier, preferably in sealing abutment against the bore. Plastic material is then injected into the gap remaining between the two parts and completely fills the gap and connects the bristle carrier to the holding part. The intermediate layer formed thereby is in the form of an insert molding preferably not only disposed between the bristle carrier and the plate. It can also entirely or in part circumferentially surround the plate and/or the bristle carrier. For example, an abutment edge can thereby be produced from a different material which encloses the bristle carrier and the holding part circumferentially and defines the outer contour. The injected material is usually a thermoplastic material. This plastic material can be soft elastic material. Alternatively, the injected material can be formed from a hard component, for example, PP, PE, PA, POM, PC or PBT. Generally preferable is easy-flowing plastic material, preferably plastic material with an MFI>15 g/10 min at 2.16 kg and a test temperature corresponding to the plastic material. It is also possible to add to the injected material an additive which has a cleaning or polishing effect so that the teeth or tissue regions within the oral cavity can be gently cleaned by the outer circumference of the brush head.

According to a further preferred embodiment of the present invention, the plastic material introduced into the intermediate space overlaps or underlaps the bristle carrier or the plate, respectively. A configuration is there usually to be ensured in which the plastic material introduced into the intermediate space also transitions free of discontinuity and continuously to a surface of the bristle carrier or of the holding part, respectively. The bristle carrier can have a radial projection or radially circumferential edge which is provided spaced from the surface of the bristle carrier and is overlapped by the plastic material injected into the intermediate space in order to secure the bristle carrier also in a positive-fit manner relative to the holding part. Similarly, the plastic material injected into the intermediate space can also be provided on the underside of the plate. Also the plate can for this purpose form a radial projection which is underlapped by the solidified plastic material introduced into the intermediate space in order to also connect the plastic material introduced into the intermediate space to the holding part also in positive-fit manner in the direction of the pivot axis.

It is in view of the strongest possible connection preferable to take the plastic material introduced into the intermediate space up to the stud so that the plastic material introduced into the intermediate space substantially covers the rear side of the plate and forms the underside of the widened part of the brush head which protrudes radially to the pivot axis over the commonly cylindrical stud. The plate and the bristle carrier can there be formed with an identical base surface, where the plastic material introduced into the intermediate space is confined to precisely this intermediate space. If the plastic material inserted into the intermediate space circumferentially surrounds the bristle carrier or the plate, then the outer contour of the widened part is also, inter alia, commonly solely, defined by the plastic material introduced into the intermediate space. The plastic material introduced into the intermediate space, however, can also be disposed only below the bristle carrier so that the latter alone defines the surface penetrated by the bristle bundles and is on the rear side covered by the plate and the plastic material that is injected into the intermediate space and can also surround the plate on the rear side in order to connect the bristle carrier in a positive-fit manner to the holding part also in the direction of the pivot axis.

In view of the simplest possible production of the brush head according to the invention, it is proposed according to a preferred development of the present invention that the plate and/or the holding part form a spacer which defines the intermediate space. The respective spacer is usually integrally formed on the bristle carrier or the plate, respectively. The spacer protrudes in the direction of the pivot axis from the bristle carrier or the plate, respectively, and with its free end abuts against a counter surface which is formed by the bristle carrier or the plate, respectively. The spacer(s) can be provided on both the bristle carrier as well as on the plate in order to define the intermediate space. In the production of the brush head, the prefabricated parts bristle carrier and holding part are accordingly spaced apart in the injection mold by way of the spacers, but are already pressed against one another, which can lead to a certain deformation of the spacers. However, the intermediate space which always remains is filled with the plastic material introduced into the intermediate space during insert molding, so that a brush head with predetermined dimensions can be produced not least due to the spacers.

The height of the intermediate space preferably corresponds approximately to the size of the thickening in order to set the height of the brush head as compact as possible. This criterion is already fulfilled where the height corresponds to 80 to 200% of the height extension of the thickening.

According to a further preferred embodiment of the present invention, nubs are provided on the rear side of the plate, i.e. on the side facing away from the bristle carrier, and are preferably integrally formed on the holding part. The free ends of these nubs are exposed on the undersurface of the brush body. The nubs usually extend parallel to the pivot axis. The aforementioned nubs also serve to position the plate in an injection mold in such a manner that the plastic material introduced into the intermediate space can flow around the underside of the plate and solidify there, so that this underside is substantially entirely formed by the plastic material introduced into the intermediate space and only the nubs with their free ends are exposed on this undersurface. A predetermined layer thickness of the plastic material introduced into the intermediate space on the underside of the brush head is thereby defined in a simple manner. The spacing required for this purpose in the injection molding material is reliably and simply set by the nubs. The nubs are usually disposed in radial direction within an outer edge of the plate so that the latter can at the edge be configured relatively thin and can be enclosed by the plastic material introduced into the intermediate space.

The abovementioned spacers and/or nubs are usually provided distributed in the circumferential direction on the upper surface or the undersurface of the bristle carrier and/or the plate, respectively.

The present invention also relates to an attachment part for an electric toothbrush comprising a sleeve member, a drive shaft provided therein, which can be coupled to a drive of the electric toothbrush, and a brush head according to the present invention. The brush head is there coupled to the drive shaft. The sleeve member at its end disposed opposite to the brush head comprises mechanical connection options for holding the attachment part on the handpiece of the electric toothbrush. Furthermore, the drive shaft is at the end side configured such that the drive shaft is coupled to the drive shaft of the handpiece when the sleeve member is attached onto the housing of the handpiece of the electric toothbrush in order to transmit the rotational motion of the drive shaft to the brush head. The brush head is there commonly pivoted, i.e. the drive shaft is not driven in a rotational manner but is only pivoted cyclically by a certain angular range.

BRIEF DESCRIPTION OF THE DRAWINGS

Further details and advantages of the present invention shall become apparent from the following description of embodiments in combination with the drawing, in which.

DETAILED DESCRIPTION OF THE INVENTION

Figure 1:
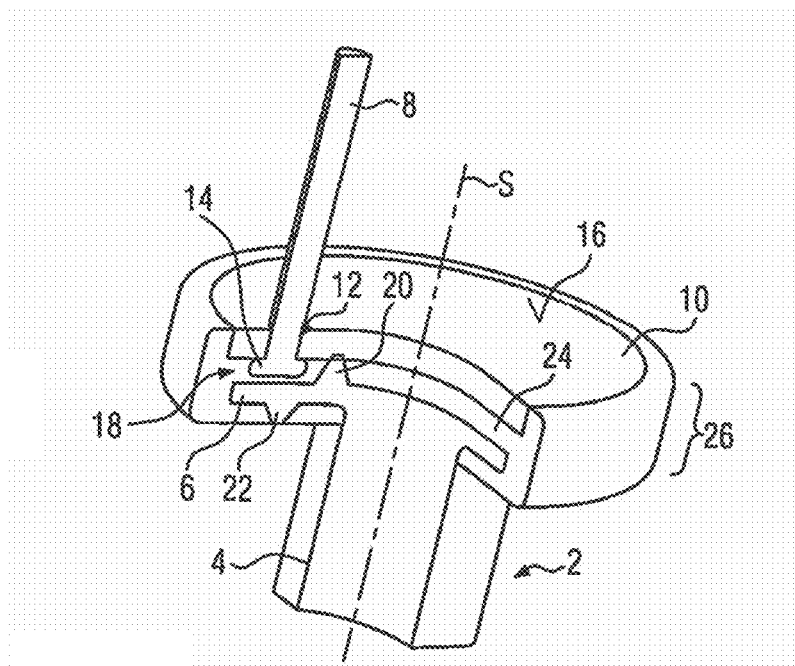
FIG. 1 is a perspective, partially sectional view of a first embodiment of the present invention.

The figures each schematically illustrated the embodiments. Reference numeral 2 denotes a holding part which forms a stud 4 and a plate 6 protruding radially therefrom and provided integrally on the stud 4. A bristle bundle 8 penetrates a bore 12 provided in a bristle carrier 10 and with its thickening 14 abuts at the rear side of the bristle carrier 10 against the latter. To simplify the illustration, only one bristle bundle 8 is shown in FIG. 1. It goes without saying that the entire surface 16 being formed by the bristle carrier 10 is protruded by bristle bundles or other cleaning elements, for example, TPE cleaning elements, in order to achieve a cleaning effect over the entire surface. The bristle bundles and the cleaning elements can have different diameters, colors, material properties and contours as well as different bristle filaments and a different number of bristle filaments, as is customary in the market. Suitable cleaning elements are, in particular, TPE cleaning elements which extend substantially parallel to the bristle bundle 8. Such TPE elements can also be attached to the bristle carrier 10 in an articulate manner.

Reference numeral 18 denotes an intermediate space enclosed between the underside of the bristle carrier 10 and the upper side of the plate 6. Projecting into this intermediate space 18 is a spacer 20 protruding from the plate and abutting against the underside of the bristle carrier 10 and holding the latter at a predetermined distance from the plate 6. FIG. 1 illustrates only one such spacer 20, although several such spacers 20 protrude from the surface of the plate 6 in order to hold and support the bristle carrier 10 in a punctiform manner but at various locations relative to the plate 6.

A nub 22 protrudes from the underside of the plate 6. Several of these nubs 22 are also provided on the underside of the plate 6 and formed integrally thereonto.

Reference numeral 24 denotes plastic material that is injected into the intermediate space 18. It entirely fills the intermediate space 18. The plastic material 24 also surrounds the bristle carrier 10 circumferentially, but ends on the surface 16 flush with the bristle carrier 10. The plastic material 24 also surrounds the underside of the plate 6 and extends radially up to the stud 4. A widened part of the brush head denoted with reference numeral 26 is in this embodiment formed in the manner of a disc which is composed of the bristle carrier 10, the plate 6, and the injection molded plastic material 24. The edges of the disc are each rounded. The plastic material 24 is presently an easily flowing thermoplastic elastomer which not only connects the bristle carrier 10 to the plate 6 but also forms an outer-side boundary of the disc from relatively soft material which is gentler to the tender oral mucosa than harder plastic material.

The holding part 2 is formed from technical plastic material. Technical plastic material exhibits high wear resistance and a high modulus of elasticity of at least 1500 MPa. The viscosity of such technical plastic material is relatively high. The MFI of a technical plastic material of the present invention is at ≤20 g/10 min at the test temperature corresponding to the plastic material and a load of 2.16 kg. A technical plastic material is, in particular, POM, PA, PC, or PBT. The holding part 2 is made of such material. The stud 4 commonly comprises the connections, holders and centering devices presented in the general description with which the embodiment shown can be held in a sleeve member (not shown) of an attachment part for an electric toothbrush and can be mechanically coupled to the drive.

In the embodiment shown, the plastic material 24 can impart adhesion between the bristle carrier 10 and the holding part 2 made of the technical plastic material. The bristle carrier can there be formed from a hard component, for example, PA, PET, PP, PE, POM, PC, or PBT, respectively.

The embodiment shown in FIG. 1 assumes that a positive-fit connection is necessary for reliable attachment of the plastic material 24 to the holding part 2. The plastic material 24 also extends on the underside of the plate and accordingly forms the undersurface of the widened part 26 which is penetrated by the stud 4. The material nature of the bristle carrier 10, however, is such that the plastic material 24 can only in a positive substance-fit manner be reliably bonded to the bristle carrier 10. The plastic material 24, however, surrounds the bristle carrier 10 merely circumferentially.

To produce the embodiment shown in FIG. 1, the bristle carrier 10 is first produced from plastic material by way of injection molding, where the bore 12 or the bores are formed during injection molding. The bristle carrier 10 is thereafter provided with the bristle bundles 8, the attachment-side end being initially arranged at a distance from the bristle carrier 10 and being melted to form the thickening 14. The bristle bundle 8 is then displaced axially in order to abut the thickening 14, formed during the surface melting process, against the underside of the bristle carrier 10.

The holding part 2 is by injection molding prepared from the technical plastic material in the final contour with all functional surfaces on the stud 4. The two prepared components 2 and 10 are placed into an injection mold. The holding part 2 is there assigned to the one mold half, and the bristle carrier 10 to the other mold half. The bristle carrier 10 is there commonly held by a so-called perforated field plate which is usually outside the injection mold provided with the bristle carrier 10 and thereafter for completion of the injection mold inserted into the latter. When the injection mold is closed, the spacers 20 are abutted against the underside of the bristle carrier 10 and are there slightly compressed. The remaining intermediate space 18 is filled with the plastic material 24 that is then injected. The otherwise flat rear side of the plate 6 is by the nubs 22 held at a distance from the injection mold so that a gap remains there that is filled with the plastic material 24 in order to form the rear-side injection molding of the plate with the plastic material 24. After sufficient cooling of the plastic material 24, the mold nest is opened and the completed product shown schematically in FIG. 1 is taken out.

Figure 2:
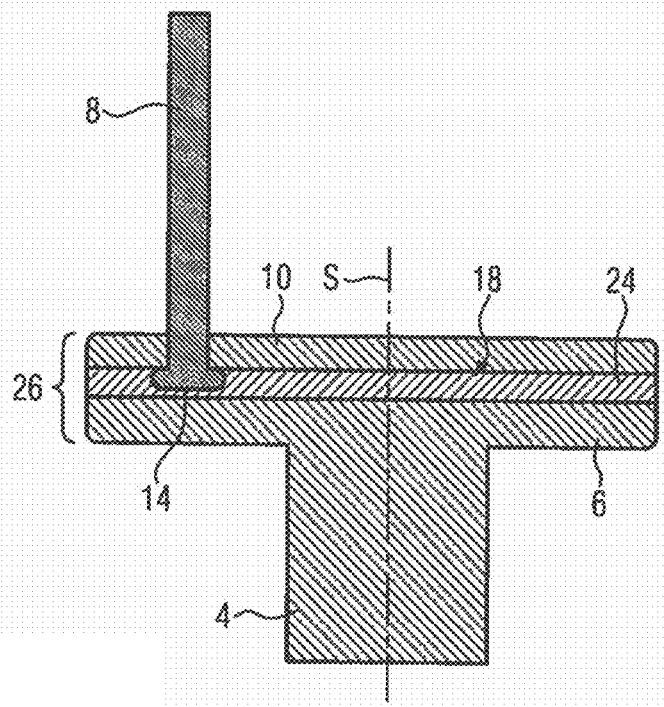
FIG. 2 is a cross-sectional view of a second embodiment.

FIG. 2 shows a cross-sectional view of a basic form of the present invention. Identical components are marked with the same reference symbols as in the previously described embodiment. This applies to all the figures of the drawing.

In the basic form according to FIG. 2, the intermediate space 18 is filled with the plastic material 24. The plastic material 24 ends flush with an outer circumferential surface of the widened part 26 which is formed at the top by the edge of the bristle carrier 10, at the bottom by the edge of the plate 6 and therebetween by the plastic material 24.

Figure 3:
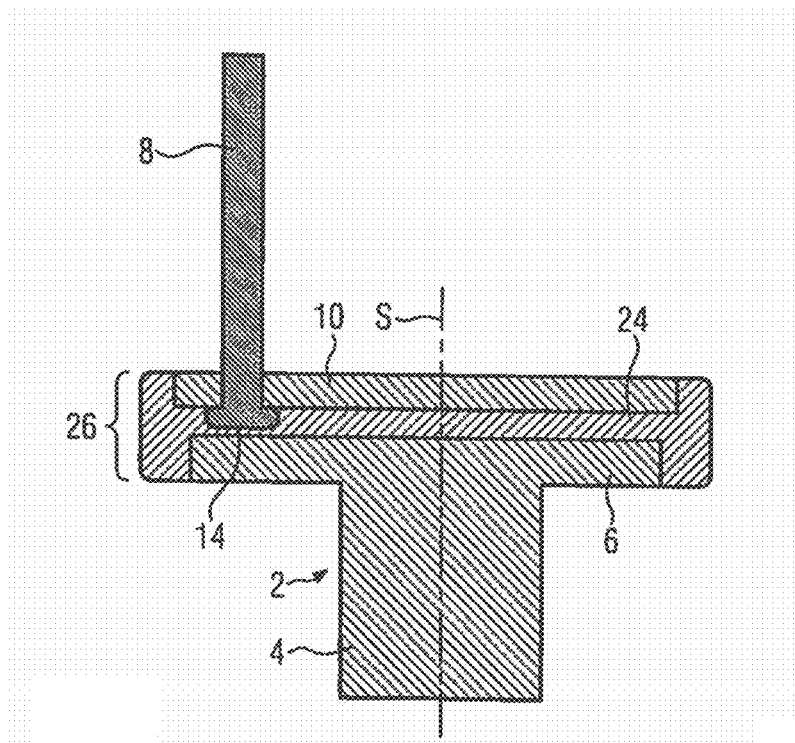
FIG. 3 is a cross-sectional view of a third embodiment.

In the embodiment according to FIG. 3, the plate 6 has a smaller radial extension than the bristle carrier 10 as compared to FIG. 2. The plastic material 24 circumferentially surrounds both the bristle carrier 10 as well as the plate 6 but does not contribute anything to a higher thickness above the surface 16 or below the underside of the plate 6, respectively. The plastic material 24 is merely an impact protection which surrounds the bristle carrier 10 and the plate 6 circumferentially. In such a configuration, the holding part 2 and the bristle carrier 10 are usually formed from plastic materials which adhere to the plastic material 24 that is injected into the intermediate space 18, so that a positive substance-fit connection arises in the direction of the pivot axis S.

Figure 4:
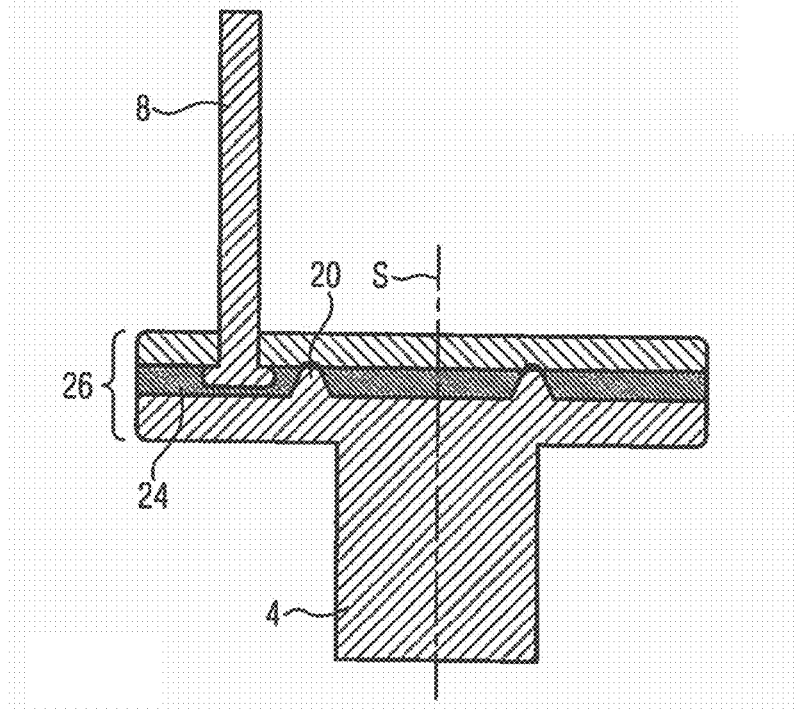
FIG. 4 is a cross-sectional view of a fourth embodiment.

The embodiment shown in FIG. 4 substantially corresponds to FIG. 2, where, however, the spacers 20 formed integrally on the holding part 2 protrude from the plate 6 and abut against the underside of the bristle carrier 10 in order to define the intermediate space 18.

Figure 5:
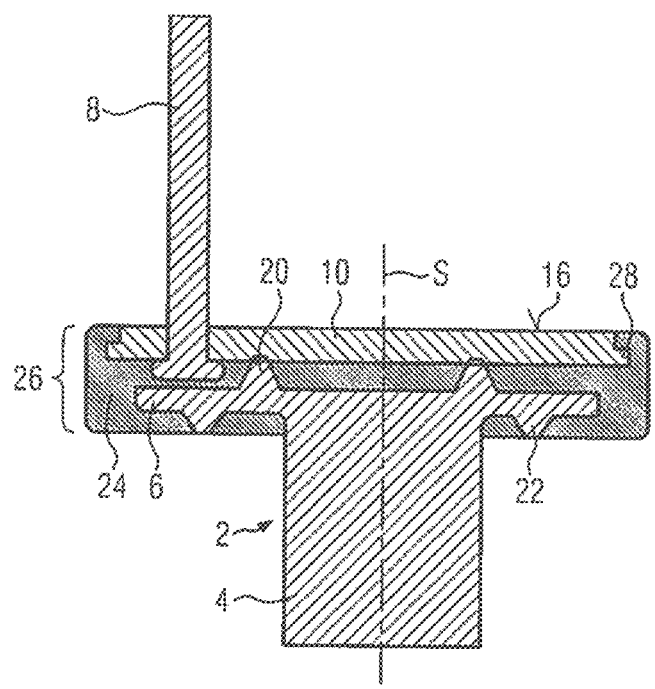
FIG. 5 is a cross-sectional view of a fifth embodiment.

The configuration shown in FIG. 5 substantially corresponds to the example according to FIG. 1. However, the bristle carrier 10 there has a locking edge 28 being formed spaced from the surface 16 and radially projecting over the surface 16 formed by the bristle carrier 10 and being protruded by the plastic material 24 in the direction of a pivot axis marked with reference symbol S. As a result, also the bristle carrier 10 is in a positive-fit manner secured against being pulled out in the direction of the pivot axis S. Due to the underside of the plate 6 being underlapped, a correspondingly acting positive-fit connection is established between the plastic material 24 and the holding part 2. In addition, the plastic material 24 surrounds both the bristle carrier 10 as well as the plate 6 at the outer circumference so that a positive-fit connection is given also in a direction that is radial to the pivot axis S. The embodiment shown in FIG. 5 is particularly suitable for connecting the various components when the material of the bristle carrier 10 and the material of the holding part 2 are incompatible with the plastic material 24 in terms of adhesion.

Figure 6:
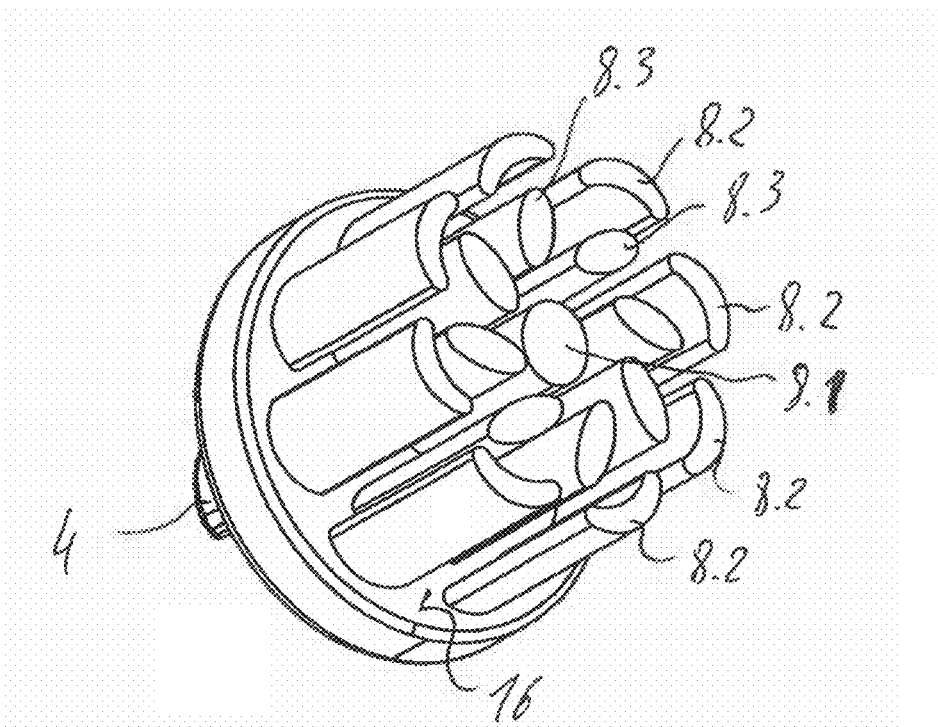
FIG. 6 is a perspective side view of a top side of a sixth embodiment of the present invention.
Figure 7:
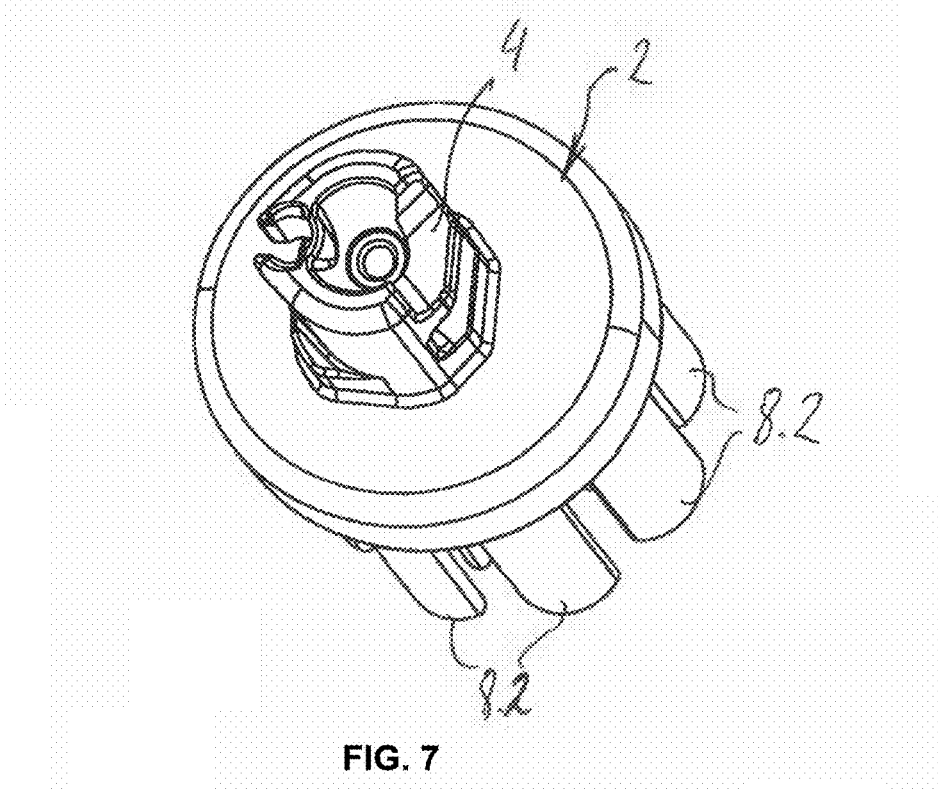
FIG. 7 is a perspective side view of a bottom side of sixth embodiment of the present invention.

The brush head depicted in FIGS. 6 and 7 show a specific embodiment with sickle-shaped bristle bundles surrounding a round central bristle bundle 8.1. While the central bristle bundle 8.1 is composed of between 320 and 400 filaments, the sickle-shaped bristle bundles are made of between 160 and 200 filaments, each of which have a size of 5 mil i.e 0.127 mm. Eight outer sickle-shaped bristle bundles 8.2 are circumferentially spaced apart from each other at the outer circumference with an essentially circumferential extension, while intermediate sickle-shaped bristle bundles 8.3 are arranged radially inwardly thereof and between the central bristle bundle 8.1 and the outer sickle-shaped bristle bundles 8.2. Those intermediate sickle-shaped bristle bundles 8.3 have a rather radial extension. In other words, the longitudinal axis of the longitudinal sickle-shaped bristle bundles 8.3 extend essentially in a radial direction.

Figure 9:
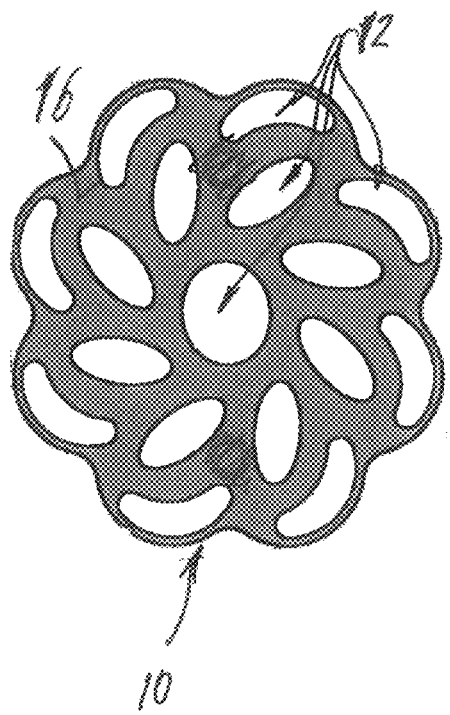
FIG. 9 is a top view of the bristle carrier depicted in FIG. 8.
Figure 8:
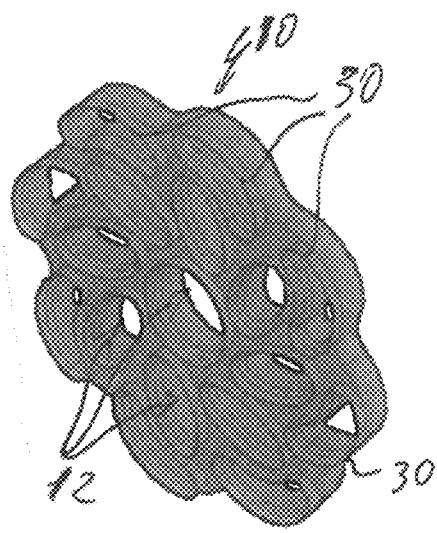
FIG. 8 is a perspective side view of the bristle carrier of the sixth embodiment.
Figure 10:
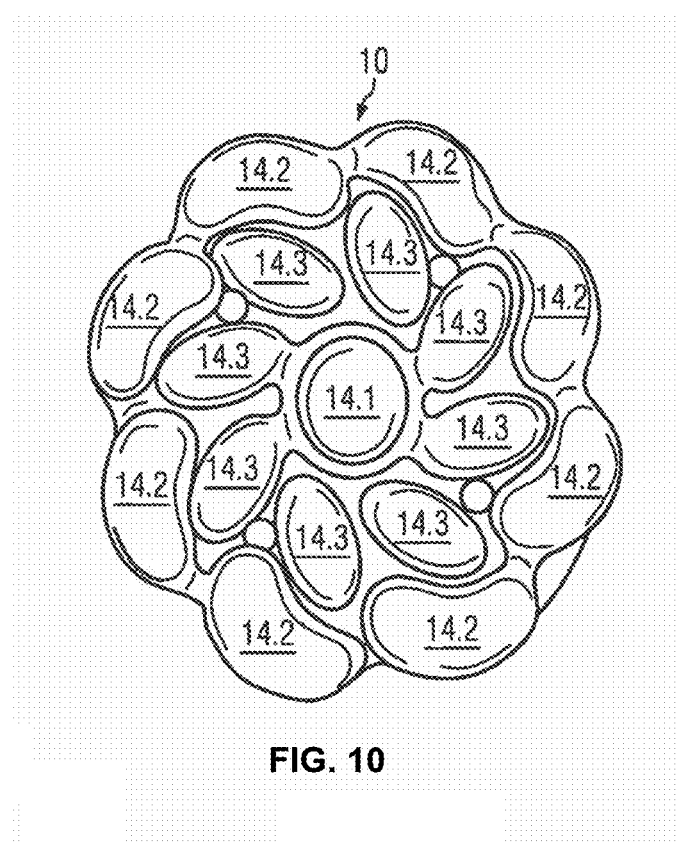
FIG. 10 is a top view corresponding to FIG. 9 after tufting and securing bristle bundles against the bristle carrier by melting.

The specific geometry of the bristle bundles 8 of this sixth embodiment is derivable from the top view of the bristle carrier 10 depicted in FIG. 9. This bristle carrier 10 has multiple bores 12 corresponding in geometry with the size of each bristle bundle 8. The rear surface of the bristle carrier 10, i.e. the main surface of the bristle carrier 10 facing towards the holding part 6 shows rims encircling each bore 12, which rims are identified with reference numeral 30. The rims each project from an essentially flat surface, which surface defines the rear surface of the bristle carrier 10. When preparing the bristle bundles 8, the same are inserted into the bristle carrier 10 and melted such that the melt generated by each bristle bundle 8 contacts the circumferential rim 30 of a respective bore 12 assigned to a respective bristle bundle 8 to contact, preferably join by welding, the bristle bundle 8 against the bristle carrier 10, namely against the circumferential rim 30 of the assigned bore. The product received is depicted in FIG. 10, which shows the rearward surface of the bristle carrier 10 with a thickening 14 clearly visible for each bristle bundle. The thickening for the outer bristle bundles 8.2 are identified with reference numeral 14.2. The thickening for the central bristle bundle 8.1 is identified with reference numeral 14.1. The intermediate thickenings 14.3 are assigned to the respective intermediate bristle bundles 8.3. After melting the bristle bundles 8 against the bristle carrier 10, the surface thereof is essentially free of gaps, preferable completely sealed.

Figure 11:
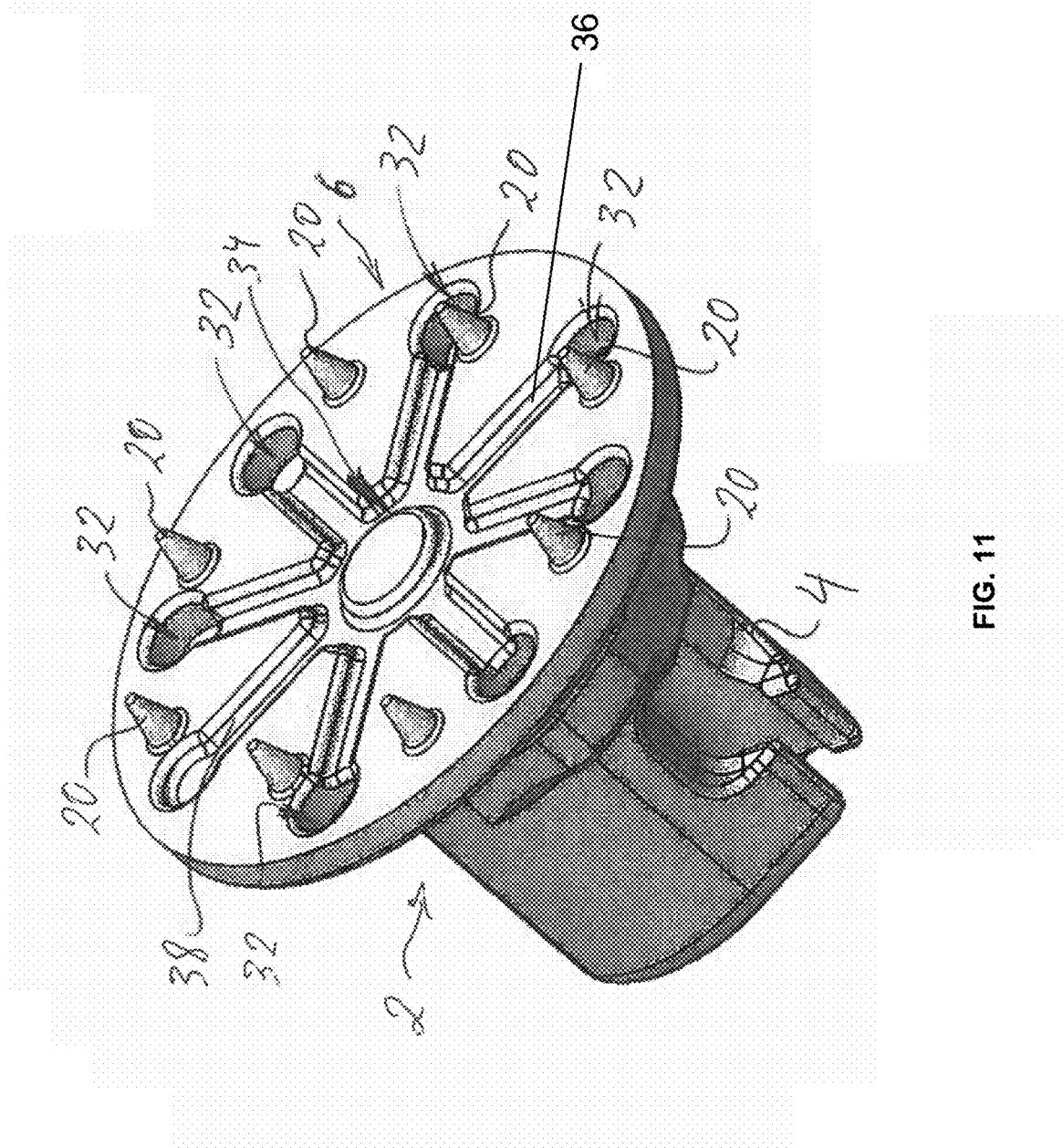
FIG. 11 is a perspective side view of the holding part of the sixth embodiment.

The plate 6 of the holding part 2 depicted in FIG. 11 has multiple through-holes 32 extending parallel to the stud 4, which projects from the back surface of the plate 6. Those through-holes 32 are disposed between conical spacers 20, which project the plate 6. From a ring-shaped central channel 34 recessed in the upper surface of the plate 6, radial channels 36 extend in radial direction and generally terminate at the through-hole 32. A channel identified with reference numeral 38 is not assigned to a respective through-hole.

When placing the holding part 2 and the tufted bristle carrier 10 in an injection molding tool, an intermediate space is held free by the conical spacers 20 cooperating with the rearward surface of the bristle carrier 10. As the spacers 20 are conical, a holding force of the injection molding tool may deform the tip portion of the spacer 20 depending on the surface configuration of the thickening 14, which is not exactly controlled and results from solidification of the melt formed by the bristle bundles 8. Thereafter and as already described for the previous embodiments, plastic melt is injection-molded into the intermediate space to join the holding part 2 and the bristle carrier 10. Such melt will be allowed to thoroughly distribute in the intermediate space 18 and at the rearward surface of the plate 6 as the melt can pass through the plate 6 through the through-holes 32. In the present embodiment, the plastic material is injected from the rear, i.e. lower side of the plate 6 to flow around the outer circumference thereof and through the through-holes 32. The plastic material will flow in the intermediate space 18 assisted by the radial channels 36, 38 and the central channel 34 to equally distribute in the intermediate space and will flow around the bristle carrier 10. However, as in the previous embodiment, the surface 16 of the bristle carrier 10 will form the surface of the final brush head being projected by the bristle bundles 8.

LIST OF REFERENCE NUMERALS 2 holding part
4 Stud
6 Plate
8 bristle bundle
8.1 central bristle bundle
8.2 outer sickle-shaped bristle bundle
8.3 intermediate bristle bundle
10 bristle carrier
12 bore
14 thickening
14.1 central thickening
14.2 outer thickening
14.3 intermediate thickening
16 surface
18 intermediate space
20 spacer
22 nub
24 plastic material injected into the intermediate space 18
26 widened part
28 locking edge, widened part of the brush head
30 circumferential rim
32 through-hole
34 central channel
36 radial channel
38 radial channel without through-hole
S pivot axis

The invention claimed is:

1. A brush head for an electrically driven toothbrush, comprising:
a holding part (2) that provides at least one connecting element for mechanically coupling said brush head to the electric drive of said toothbrush, wherein said holding part (2) integrally forms a stud (4) defining a pivot axis (S) about which said brush head is pivotable and a plate (6) which at an end thereof facing away from said stud (4) carries at least one bristle bundle (8) which at an attachment-side end comprises a thickening (14) formed by melting a material forming the bristle bundles (8); and
a substantially disc-shaped bristle carrier (10) comprising a bore that is penetrated by said bristle bundle (8) and being connected to said holding part (2),
wherein said bristle carrier (10) is connected to said holding part (2) by a plastic material (24) inserted into an intermediate space (18) between said bristle carrier (10) and said holding part (2), and
wherein the thickening (14) at the attachment-side end of the bristle bundle (8) is substantially surrounded by the plastic material (24).

2. The brush head according to claim 1, wherein said plastic material (24) introduced into said intermediate space (18) circumferentially surrounds said bristle carrier (10) or said plate (6).

3. The brush head according to claim 1, wherein said plastic material (24) introduced into said intermediate space (18) circumferentially surrounds said bristle carrier (10) and said plate (6).

4. The brush head according to claim 1, wherein said plastic material (24) introduced into said intermediate space underlaps and overlaps said plate (6) or said bristle carrier, respectively.

5. The brush head according to claim 1, wherein said plastic material (24) introduced into said intermediate space underlaps and overlaps said plate (6) and said bristle carrier.

6. The brush head according to claim 1, wherein said bristle carrier (10) or said holding part (2) forms a spacer (20) which defines said intermediate space.

7. The brush head according to claim 6, wherein said intermediate space corresponds approximately to the size of said thickening (14).

8. The brush head according to claim 1, wherein said bristle carrier (10) and said holding part (2) forms a spacer (20) which defines said intermediate space.

9. The brush head according to claim 1, wherein said plastic material (24) introduced into said intermediate space (18) is provided at the underside of said plate (6).

10. The brush head according to claim 1, wherein said plastic material (24) introduced into said intermediate space (18) covers said plate (6) on the underside substantially over the entire surface.

11. The brush head according to claim 1, wherein nubs (22) that are integrally formed on said holding part (2) and the free ends of which are exposed on the undersurface of said brush head project from the rear side of said plate (6).

12. The brush head according to claim 1, wherein said plastic material (24) is TPE.

13. A brush head for an electrically driven toothbrush, comprising:
a holding part (2) that provides at least one connecting element for mechanically coupling said brush head to the electric drive of said toothbrush, wherein said holding part (2) integrally forms a stud (4) defining a pivot axis (S) about which said brush head is pivotable and a plate (6) which at an end thereof facing away from said stud (4) carries at least one bristle bundle (8) which at an attachment-side end comprises a thickening (14) formed by melting a material forming the bristle bundles (8); and
a substantially disc-shaped bristle carrier (10) comprising a bore that is penetrated by said bristle bundle (8) and being connected to said holding part (2) by a plastic material (24) injection molded into an intermediate space (18) between said bristle carrier (10) and said holding part (2), wherein said plastic material (24) introduced into said intermediate space underlaps and overlaps said plate (6) or said bristle carrier, respectively.

14. The brush head according to claim 13, wherein said plastic material (24) introduced into said intermediate space (18) circumferentially surrounds said bristle carrier (10) or said plate (6).

15. The brush head according to claim 13, wherein said plastic material (24) introduced into said intermediate space (18) circumferentially surrounds said bristle carrier (10) and said plate (6).

16. The brush head according to claim 13, wherein said plastic material (24) introduced into said intermediate space underlaps and overlaps said plate (6) and said bristle carrier.

17. The brush head according to claim 13, wherein said bristle carrier (10) or said holding part (2) forms a spacer (20) which defines said intermediate space.

18. The brush head according to claim 13, wherein said bristle carrier (10) and said holding part (2) forms a spacer (20) which defines said intermediate space.

19. The brush head according to claim 13, wherein said plastic material (24) is TPE.

20. A brush head for an electrically driven toothbrush, comprising:

a holding part (2) that provides at least one connecting element for mechanically coupling said brush head to the electric drive of said toothbrush, wherein said holding part (2) integrally forms a stud (4) defining a pivot axis (S) about which said brush head is pivotable and a plate (6) which at an end thereof facing away from said stud (4) carries at least one bristle bundle (8) which at an attachment-side end comprises a thickening (14) formed by melting a material forming the bristle bundles (8); and a substantially disc-shaped bristle carrier (10) comprising a bore that is penetrated by said bristle bundle (8) and being connected to said holding part (2), wherein said bristle carrier (10) is connected to said holding part (2) by a plastic material (24) inserted into an intermediate space (18) between said bristle carrier (10) and said holding part (2), and wherein said bristle carrier (10) or said holding part (2) forms a spacer (20) which defines said intermediate space.

21. The brush head according to claim 20, wherein said plastic material (24) introduced into said intermediate space (18) circumferentially surrounds said bristle carrier (10) and said plate (6).

22. The brush head according to claim 20, wherein said bristle carrier (10) and said holding part (2) forms a spacer (20) which defines said intermediate space.

* * * * *